United States Patent [19]

Mehra et al.

[11] Patent Number: 5,144,960
[45] Date of Patent: Sep. 8, 1992

[54] TRANSVENOUS DEFIBRILLATION LEAD AND METHOD OF USE

[75] Inventors: Rahul Mehra, Stillwater; Paul DeGroot, Brooklyn Park; Marye S. Norenberg, Plymouth, all of Minn.

[73] Assignee: Medtronic, Inc., Minneapolis, Minn.

[21] Appl. No.: 672,285

[22] Filed: Mar. 20, 1991

[51] Int. Cl.$^5$ .................. A61N 1/05; A61N 1/39
[52] U.S. Cl. .................. 128/786; 128/419 D; 128/785
[58] Field of Search ............. 128/783, 784, 785, 786, 128/419 D, 642

[56] References Cited

U.S. PATENT DOCUMENTS

| | | | |
|---|---|---|---|
| Re. 27,757 | 3/1987 | Mirowski | 128/419 D |
| 3,729,008 | 4/1973 | Berkovits | 128/419 P |
| 3,866,615 | 2/1975 | Hewson | 128/419 D |
| 3,942,536 | 3/1976 | Mirowski | 128/419 D |
| 4,106,512 | 8/1978 | Bisping | 128/419 P |
| 4,161,952 | 7/1979 | Kinney et al. | 128/786 |
| 4,289,138 | 9/1981 | Halvorsen | 128/786 |
| 4,355,646 | 10/1982 | Kallok et al. | 128/786 |
| 4,402,330 | 9/1983 | Lindemans | 128/786 |
| 4,481,953 | 11/1984 | Gold et al. | 128/786 |
| 4,567,901 | 2/1986 | Harris | 128/786 |
| 4,641,656 | 2/1987 | Smits | 128/419 D |
| 4,708,145 | 11/1987 | Tacker, Jr. et al. | 128/419 D |
| 4,727,877 | 3/1988 | Kallok | 128/419 D |
| 4,817,634 | 4/1989 | Halleman et al. | 128/784 |
| 4,934,049 | 6/1990 | Kiekhafer et al. | 128/786 |
| 4,951,687 | 8/1990 | Ufford et al. | 128/786 |
| 4,953,551 | 9/1990 | Mehra et al. | 128/419 D |
| 4,998,975 | 3/1991 | Cohen et al. | 128/419 D |
| 5,044,375 | 9/1991 | Bach, Jr. et al. | 128/786 |

FOREIGN PATENT DOCUMENTS 0006148  7/1989  PCT Int'l Appl. ............ 128/785

*Primary Examiner*—William E. Kamm
*Assistant Examiner*—Kennedy J. Schaetzle
*Attorney, Agent, or Firm*—Reed A. Duthler; Harold R. Patton

[57] ABSTRACT

An implantable transvenous defibrillation/cardioversion lead. The lead extends from a proximal end carrying electrical connectors to a bifurcated distal end. Distal to the bifurcation are a first, generally straight leg and a second, curved leg. In use, the distal end of the first, generally straight leg is located in the apex of the right ventricle and the distal end of the second, generally curved leg is located in the outflow tract from the right ventricle, with the point of bifurcation located approximately adjacent the tricuspid valve. Elongated coil electrodes are provided extending along the straight and curved legs, distal to the point of bifurcation of lead. The lead may be used in conjunction with a subcutaneous or othe additional defibrillation/cardioversion electrode.

10 Claims, 2 Drawing Sheets

TRANSVENOUS DEFIBRILLATION LEAD AND METHOD OF USE

BACKGROUND OF THE INVENTION

The present invention relates to medical electrical leads generally, and more particularly to implantable defibrillation electrodes and leads.

Early concepts of implantable defibrillators, such as disclosed in Reissue U.S. Pat. No. 27,652 by Mirowski et. al., envision an electrode system employing a ventricular endocardial electrode and a plate electrode mounted to the heart directly, subcutaneously, or to the skin. However, it has long been recognized that a totally transvenous system would be desirable in order to simply the use of implantable defibrillators. Once such system is suggested in U.S. Pat. No. 3,942,536 by Mirowski et. al., which discloses a transvenous lead having electrodes intended for location in the right ventricular apex and in the superior vena cava. Such systems were eventually tested in human beings, with some success. However, currently available implantable defibrillators typically employ epicardial patch electrodes, alone, or in conjunction with transvenous electrodes.

While systems employing epicardial patch electrodes are workable, a thoracotomy is required in order to apply the epicardial electrodes. It is generally believed that it would be desirable to produce an implantable defibrillation system which entirely avoids the necessity of a thoracotomy, and there has been substantial work directed towards development of such systems, as disclosed in U.S. Pat. No. 4,727,877 issued to Kallok, U.S. Pat. No. 4,708,145 issued to Tacker et al. and as disclosed in U.S. application Ser. No. 07/284,957 filed Dec. 15, 1988 by Mehra, for an "Endocardial Defibrillation Electrode System". Other endocardial defibrillation electrodes are disclosed in U.S. Pat. No. 4,481,953 issued to Gold et al., U.S. Pat. No. 4,481,953 issued to Kinney et al., U.S. Pat. No. 4,934,049 issued to Kiekhafer et al. and in U.S. patent application Ser. No. 07/479,928, filed Feb. 14, 1990 by Holleman et al., for an "Implantable Electrode and Method for Fabrication". The Kinney, Gold and Kiekhafer patents and the Holleman et al. application all disclose endocardial defibrillation leads employing defibrillation electrodes fabricated from elongated coils of biocompatible metal, mounted exposed to the exterior of the defibrillation lead, for location in the right ventricle and other locations within the heart. U.S. Pat. No. 4,641,656 issued to Smits and the above cited Mehra application both disclose a variety of endocardial defibrillation electrodes intended for use in the atrium, ventricle and coronary sinus, all of which employ electrodes taking the form of elongated coils of conductive biocompatible metals.

SUMMARY OF THE INVENTION

The present invention is directed toward the provision of an endocardial defibrillation lead particularly optimized for use in conjunction with one or more epicardial patch or subcutaneous patch electrodes. However, the electrode may also possibly be used in conjunction with other endocardial electrodes, such as superior vena cava or coronary sinus electrodes.

The lead is provided with a bifurcated body, including a first, generally straight leg lying along the axis of the lead body and a second curved leg diverging from the axis of the lead body. In use, the lead is inserted into the right ventricle such that the distal end of the straight leg is located at the ventricular apex and the distal end of the curved leg is located in the outflow tract of the right ventricle. Each of the two legs is provided with an electrode taking the form of an elongated coil of biocompatible, conductive metal, exposed to the exterior of the lead body.

In use, it is envisioned that the electrode on the curved leg and the electrode on the straight leg of the lead will be coupled together, and defibrillation pulses delivered between these two electrodes and one or more subcutaneous or epicardial electrodes. The electrode design allows for an endocardial electrode which is widely distributed within the right ventricle, providing for a substantial increase in electrode surface area and distributing the surface area more widely, with respect to the left ventricle. This improvement in the electrode configuration is believed to be helpful in improving the current distribution between the electrode and associated epicardial or subcutaneous electrodes. In its preferred embodiment, the electrode is used with only a single additional electrode, located subcutaneously, thus simplifying the implant procedure required to use the lead.

The distal end of the straight leg of the lead is provided with a bipolar electrode pair, the distal electrode taking the form of an endocardial screw-in electrode similar to those used in prior art endocardial screw-in pacing leads. This electrode serves to anchor and locate the lead. The curved leg of the lead is simply provided with a rounded, insulated end portion, and is maintained in this position solely as a result of its attachment to the remainder of the lead body and its inherent curved configuration. This approach is believed to be substantially superior to the approach illustrated in the Smits et al patent cited above, which attempted to accomplish an increase in surface area and an improvement in electrode surface distribution within the right ventricle by means of a U-shaped electrode, having the apex of the "U" shaped curve located in the ventricular apex, and the pacing and sensing electrodes located at the distal end of the U-shaped portion of the lead body.

DETAILED DESCRIPTION OF THE PREFERRED EMBODIMENTS

Figure 1:
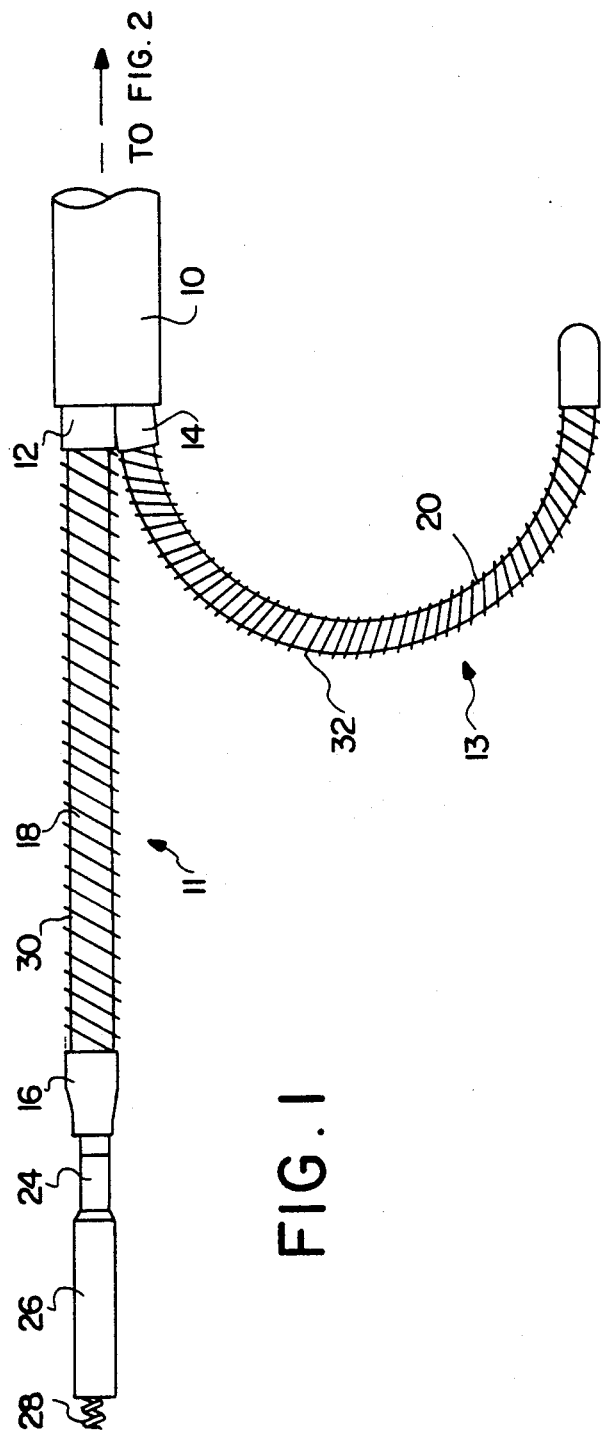
FIG. 1 illustrates the distal portion of a lead according to the present invention.

FIG. 1 illustrates the distal end of a lead according to the present invention. Mounted within outer insulative sheath 10 are two elongated tubular insulative sheaths 12 and 14, which extend through outer sheath 10, to the proximal portion of the lead. Extending distally from sheaths 12 and 14 are the straight leg 11 and the curved leg 13 of the lead, referred to above in the summary section of the application. Located on the first, straight leg 11 is a coil electrode 30, and located on the second, curved leg 13 is a corresponding coil electrode 32. The distal end of the straight leg 11 is provided with a pacing and sensing electrode assembly including an extendable helix electrode 28, mounted retractably within an insulative electrode head 26, and a ring electrode 24. A transitional insulative sleeve 16 overlaps and stabilizes the distal end of electrode coil 30.

Sheath 12 contains three concentric coiled conductors, separated from one another by tubular insulative sheaths. This tripolar arrangement is illustrated in more detail in U.S. Pat. No. 4,355,646, issued to Kallok et al. incorporated herein by reference in its entirety. As set forth in the cited Kallok et al. patent, the insulative sheaths employed in the present lead may be made of an implantable polyurethane. However, in some embodiments, the sheaths may be made of silicone rubber or other implantable, flexible plastic. The conductor coils may be made of Drawn Brazed Strand wire (DBS), previously used in cardiac pacing leads or may be another implantable metal such as MP35N alloy, also commonly used in pacing leads.

The outermost of the three conductor coils within sheath 12 is coupled to the proximal end of electrode coil 30 and the middle coil within sheath 12 is coupled to ring electrode 24. As illustrated, insulative sheath 18, around which electrode 30 is mounted also serves to insulate the outermost of the three conductor coils from the middle coil, while sheath 12 surrounds the outermost coil. The innermost coil is mounted rotatably within an insulative sheath separating the innermost coil from the middle coil, and is mechanically and electrically coupled to helix electrode 28, which is retractably mounted within electrode head 26. Rotation of the innermost conductor coil causes rotation of electrode 28 and advancement of electrode 28 out the distal end of electrode head 26. Electrode 28 may be screwed into the tissue of the right ventricle of the heart, and is used to anchor the lead. The electrode head 26, electrode 28, and the inner most conductor coil employed to rotate the helical electrode 28 are described in more detail in U.S. Pat. No. 4,106,512, issued Aug. 15, 1978 to Bisping, incorporated herein by reference in its entirety.

Insulative sheath 14 contains a single coiled conductor, coupled to the proximal end of electrode coil 32. This conductor coil may optionally extend within sheath 32 to the proximal end of the curved leg of the lead, and may also be coupled to the distal end of the electrode 32. At the distal end of the curved leg of the lead is an insulative plastic tip 22.

Electrodes 30 and 32 may be mounted around insulative sheaths 18 and 20 and bonded to these sheaths by means of a backfill of insulative plastic, as described in U.S. Pat. No. 4,934,049 issued to Kiekhafer et al. on Jun. 19, 1990, and incorporated herein by reference in its entirety. As an alternative, the insulative sheaths 18 and 20 may be fabricated of a polyurethane or other heat flowable material, expanded against the interior of the electrode coils under pressure and heated to allow the material of the sheath to flow between the electrode coils, as illustrated in U.S. patent application Ser. No. 07/479,928, filed on Feb. 14, 1990 for an "Implantable Electrode and Method for Fabrication" by Holleman et al. also incorporated herein by reference in its entirety. Alternatively, the electrode coils may be fabricated using the techniques illustrated in the above cited Kinney or Gold patents. Electrodes 30 and 32 are preferably made of platinum. However, as discussed in the references cited above, other implantable metals have been disclosed for use in such electrodes.

In use, the distal end of the straight leg 11 of the lead, along which electrode 30 is mounted, is located in the right ventricular apex, and maintained in that position by means of helical electrode 28. The distal end 22 of the curved leg 13 of the lead, along which electrode 32 is mounted, is located in the outflow tract of the right ventricle. It is maintained in its location by virtue of its attachment at its proximal end to the main lead body, and by its curved configuration.

The curved configuration illustrated is maintained by any of a number of known mechanisms. It may be maintained by means of molding insulative sheath 20 in the form of a curved tube, or otherwise imparting a predetermined curve to the sheath. For example, the techniques illustrated in U.S. Pat. No. 3,729,008 issued to Berkovitz, also incorporated herein by reference in its entirety may be adapted. Alternatively, the electrode coil 32 may be preformed to exhibit a curved configuration or the conductor coil optionally located within insulative sheath 32 may be preformed to assume a curved configuration. An additional preformed curved coil devoted particularly to maintaining the curved configuration of the lead may also be used, as disclosed in U.S. Pat. No. 4,402,330, issued on Sept. 6, 1983 to Lindemans, also incorporated herein by reference in its entirety, may also be used to maintain the curved configuration.

Figure 2:
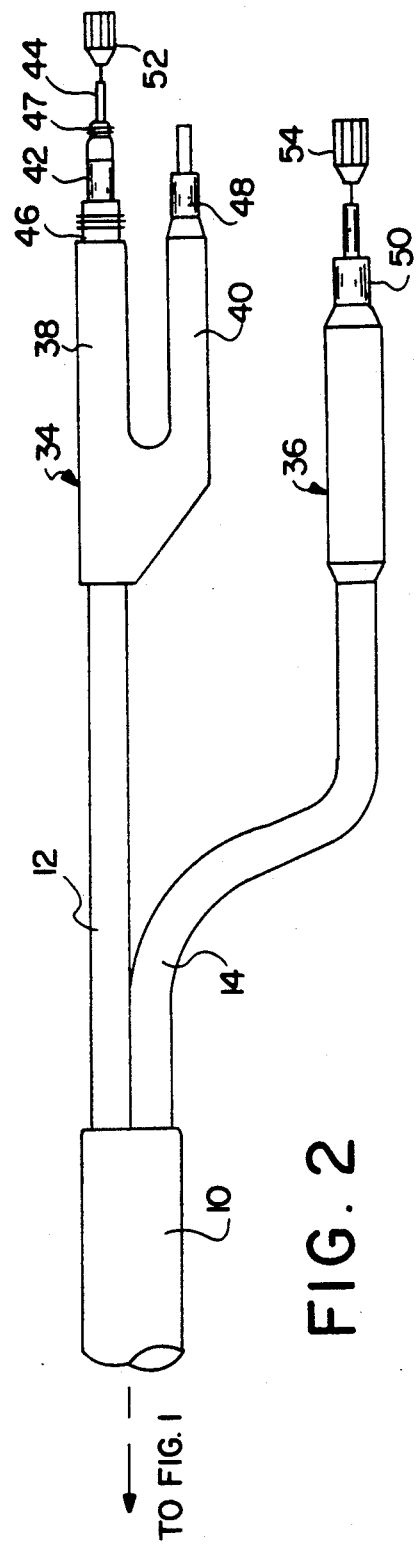
FIG. 2 illustrates the proximal portion of a lead according to the present invention.

FIG. 2 illustrates the proximal end of the lead. In this view, it can be seen that insulative sheaths 12 and 14 exit the proximal end of outer sheath 10, and extend to electrode connector assemblies 34 and 36, respectively. Electrode connector assembly 34 is a bifurcated connector, including a first connector arm 38 and a second connector arm 40.

First connector arm 38 carries a bipolar connector conforming to the international connector standard designated "IS-1". This includes a ring-shaped connector surface 42 and a connector pin 44, which is rotatably mounted within the connector arm. Also provided are insulative segments 46 and 47, which are each provided with a plurality of sealing rings for sealing the connector within the connector block of an associated implantable defibrillator. The innermost coiled conductor within sheath 12 is mechanically and electrically coupled to rotatable pin 44 such that rotation of pin 44 causes rotation of helical electrode 28 into or out of the distal end of electrode head 26. Ring electrode 42 is coupled to the middle coiled conductor within sheath 12, and is rotationally fixed. An appropriate structure for producing this IS-1 compatible, rotatable connector pin assembly illustrated may be found in U.S. Pat. No. 4,951,687 issued to Ufford et al. on Aug. 28, 1990, incorporated herein by reference in its entirety.

The outermost conductor within sheath 12 is coupled to the stepped connector pin 48 on the second arm 40 of bifurcated conductor 34. Similarly, the conductor within sheath 14, coupled to electrode 32 is coupled to a stepped connector pin 50 of configuration identical to connector pin 48.

Connector pin 44 is hollow, permitting passage of a stylet down the innermost conductive coil located within insulative sheath 12. Similarly, stepped connector pin 50 is hollow, allowing passage of a stylet 54 down the lumen of the coiled conductor within insulative sheath 14, and to the distal tip 22 of the curved leg 13 of the lead. Passage of the stylet through the straight leg 11 of the lead assists in guiding it to its appropriate location in the ventricle, and maintaining it in position while connector pin 44 is rotated to advance helical electrode 28 into the right ventricular tissue. Insertion of stylet 54 into the curved leg 13 of the lead allows for straightening of the curved configuration exhibited by electrode 32 and sheath 20, facilitating its passage through the venous system and the tricuspid valve, into the right ventricle. After the distal end of the straight leg 11 of the lead is anchored by means of electrode 28, the stylet 54 may be removed from the curved leg 13 of the lead, allowing the tip 22 to locate itself in the outflow tract of the right ventricle.

Figure 3:
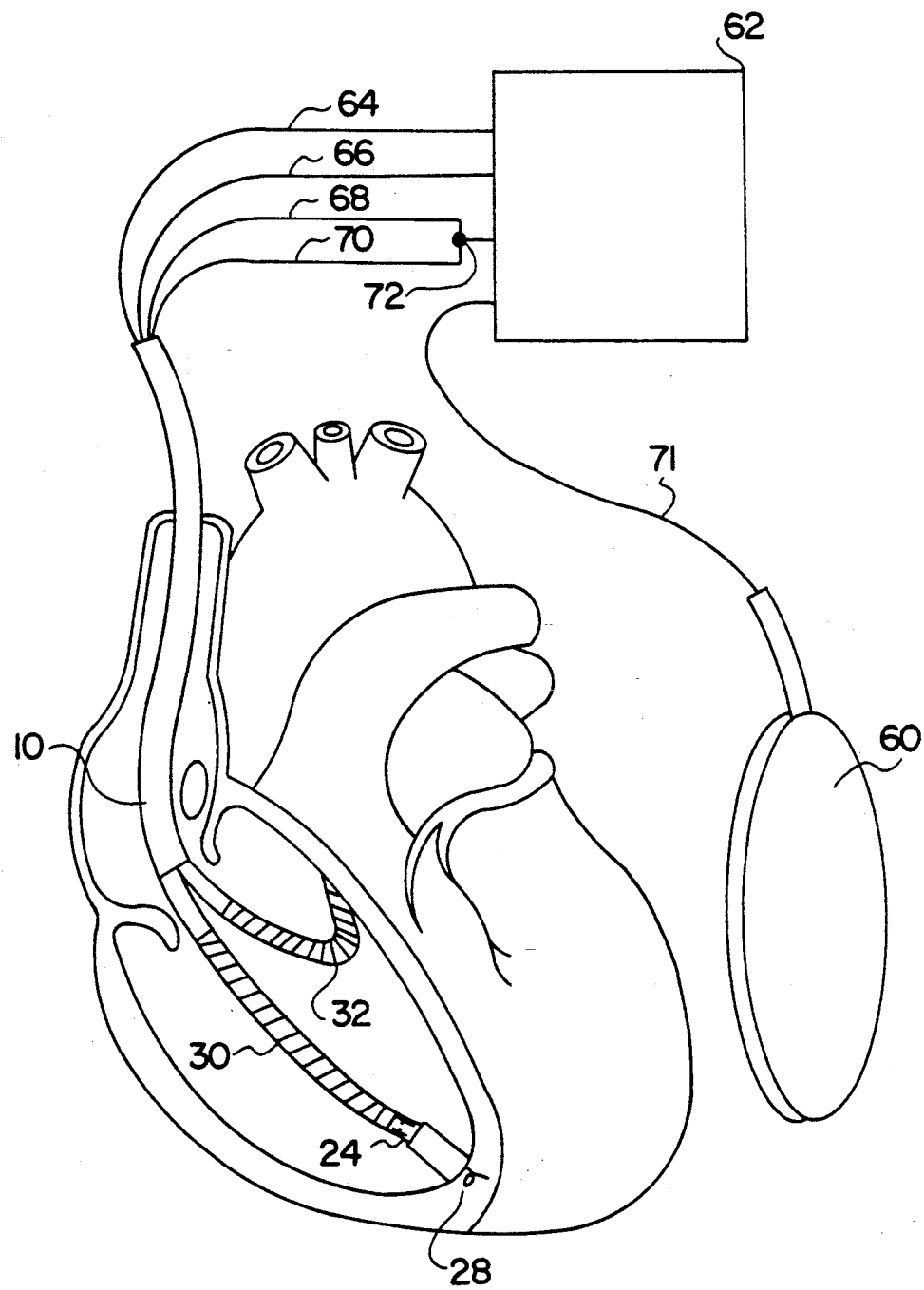
FIG. 3 illustrates a lead according to the present invention as implanted in conjunction with a subcutaneous patch electrode.

FIG. 3 illustrates the lead shown in FIGS. 1 and 2 as implanted in the right ventricle of the heart. FIG. 3 also illustrates schematically the interconnection of the electrodes on the lead and an accompanying subcutaneous patch electrode 60. As illustrated, it can be seen that the distal end of the outer sheath 10, and therefore the bifurcation point of the lead is located approximately adjacent the tricuspid valve. However, this bifurcation point may vary in hearts of differing sizes, and in some cases, it may be desirable to extend the electrode surfaces up into the right atrium of the heart.

As illustrated, the inventive lead is shown in conjunction with a subcutaneous patch electrode 60, which may correspond to any of the previously known subcutaneous patch electrodes, or may be substituted with a left ventricular epicardial electrode. Appropriate epicardial electrodes are illustrated in U.S. Pat. No. 4,817,634, issued Apr. 4, 1989 to Holleman et al. and incorporated herein by reference in its entirety. Appropriate subcutaneous electrodes may take the form of the electrodes illustrated in U.S. patent application Ser. No. 07/376,730 by Lindemans et al., filed Jul. 7, 1989 for a "patch electrode", also incorporated herein by reference in its entirety. The location of the subcutaneous electrode 60 will vary from patient to patient, depending upon the particular geometry of the patient's heart, and other considerations of bodily structure. However, generally, it can be stated that it would be desirable that the location of the subcutaneous electrode place the majority of the left ventricular mass in the electrical field established by the electrode surfaces of the right ventricular lead and the subcutaneous electrode. These considerations will generally dictate a subcutaneous electrode location on the left side of the thorax, at or somewhat below the level of the left ventricle.

In use, the electrodes on the straight and curved legs of the lead are connected in common, and a pulse is delivered between these electrodes and a subcutaneous electrode or an epicardial electrode. An implantable defibrillator 62 may be used to deliver such a pulse. A specific example of a defibrillation pulse generator which may be used in conjunction with the present lead is disclosed in U.S. Pat. No. 4,953,551, issued to Mehra et al. on Sept. 4, 1990, incorporated herein by reference in its entirety. In order to deliver this pulse regimen, it is necessary to interconnect the connectors coupled to electrodes 30 and 32. This may be accomplished either by means of a connection external to the defibrillator as in the above cited Mehra patent or may be accomplished by an internal interconnection as in U.S. patent application Ser. No. 07/612,758 for an "Apparatus for Delivering Single & Multiple Cardioversion Pulses", filed Nov. 14, 1990, by Keimel and incorporated herein by reference in its entirety.

As illustrated, conductors 64 and 66 are coupled to electrodes 24 and 28, respectively. Defibrillator 62 monitors heart activity and delivers cardiac pacing pulses via conductors 64 and 66. Conductors 68 and 70 are coupled to electrodes 30 and 32, respectively, and are coupled to one another by means of an external interconnection 72. Defibrillator 62 delivers cardioversion and defibrillation pulses between the conductor 71 coupled to electrode 60 and coupled conductors 68 and 70.

The lead disclosed herein is believed practicable in conjunction with leads which have additional features, or may delete certain features from the lead as illustrated. For example, the pacing and sensing electrodes located at the distal end of the straight leg of the lead may be in some cases omitted, or additional electrodes may be added to the lead body, for example in the portion of the lead which passes through the atrium. In addition, the curved leg 13 may extend distal to the coil electrode 20 and may include one or more electrodes for location in the right pulmonary artery for use in stimulation of the fat pads associated with the AV and SA modes of the heart. Similarly, the use of an active fixation device to anchor the straight leg of the lead may be omitted, and passive fixation means such as tines or other similar fixation mechanisms may also be employed. It may also be desirable in some cases to add fixation means for use in conjunction with the curved leg of the lead.

The connector assembly illustrated at the proximal end of the lead may also be reconfigured. For example, rather than using a bifurcated connector, a multi-polar in-line connector may also be used. Similarly, while a particular mechanism is disclosed for straightening the curved leg of the lead, other mechanisms may also be employed to accomplish this function. As such, the disclosed lead configuration should be considered exemplary, rather than limiting with regard to the interpretation of the following claims.

In conjunction with the above specification, we claim:

1. A defibrillation lead for location in a human heart, comprising:
    an elongated lead body having proximal and distal ends, having a bifurcation and having first and second legs extending distally from said bifurcation, said first leg having a generally straight configuration, said second leg having a curved configuration and constructed such that when said generally straight leg is located having a distal end at the apex of the right ventricle of said heart, a distal end of said second, curved leg may be located in the outflow tract of said heart;
    first and second elongated electrodes extending along said first and second legs, said first and second electrodes terminating proximally adjacent said bifurcation and terminating distally adjacent the distal ends of said first and second legs, respectively;
    first and second conductors located within said lead body, coupled to said first and second electrodes, respectively; and
    connector means for electrically coupling said first and second conductors to an implantable defibrillator.

2. A lead according to claim 1 further comprising means for fixing the distal end of said lead in the apex of the right ventricle of said heart.

3. A lead according to claim 2 wherein said fixing means comprises a fixation helix extending from the distal end of said first leg.

4. A lead according to claim 3 wherein said fixation helix is a pacing electrode and wherein said lead further comprises a third conductor coupled to said helical electrode.

5. A lead according to claim 1 further comprising means for straightening said second, curved leg.

6. A lead according to claim 5 wherein said straightening means comprises a stylet.

7. A method of applying cardioversion or defibrillation energy to a patient's heart, comprising:
inserting a lead having an elongated lead body with proximal and distal ends and a bifurcation intermediate its proximal and distal ends and having first and second legs extending distally from said bifurcation, said first leg having a generally straight configuration, said second leg having a curved configuration, said lead bearing first and second elongated electrodes extending along said first and second legs, the distal end of said first leg is located in the apex of the right ventricle of said heart and the distal end of said second leg is located in the outflow tract of the right ventricle of said heart;
inserting a third electrode adjacent said patient's heart; and
delivering a cardioversion or defibrillation pulse to said patient's heart via said first, second and third electrodes such that said first and second electrodes are coupled together electrically during delivery of said pulse.

8. A method according to claim 7 wherein said third electrode is inserted subcutaneously.

9. A method according to claim 7 or claim 8 wherein said lead comprises a fixation helix located at the distal end of said first leg and wherein said step of insertion of said lead comprises screwing said fixation helix into the right ventricular ape of said heart.

10. A method according to claim 7 or claim 8 wherein said step of inserting comprises straightening said second leg of said lead during insertion and thereafter allowing said second leg to return to said curved configuration such that the distal end of said second leg is located in the outflow tract of the right ventricle of said heart.

* * * * *